US012121347B1

(12) United States Patent
Majmudar et al.

(10) Patent No.: US 12,121,347 B1
(45) Date of Patent: *Oct. 22, 2024

(54) VOLUME AND INTENSITY-BASED ACTIVITY EVALUATIONS FOR DEVICES

(71) Applicant: Amazon Technologies, Inc., Seattle, WA (US)

(72) Inventors: Maulik Majmudar, Medina, WA (US); Jared Molton, Seattle, WA (US); David Robert Cole, Brier, WA (US); Hanhan Wang, Seattle, WA (US); Haithem Albadawi, Redmond, WA (US); William Scott Lamond, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/320,905

(22) Filed: May 19, 2023

Related U.S. Application Data

(63) Continuation of application No. 16/899,464, filed on Jun. 11, 2020, now Pat. No. 11,653,857.

(51) Int. Cl.
*A63B 5/02* (2006.01)
*A61B 5/024* (2006.01)
*A61B 5/11* (2006.01)
*A63B 24/00* (2006.01)

(52) U.S. Cl.
CPC ............ *A61B 5/1118* (2013.01); *A61B 5/024* (2013.01); *A63B 24/0062* (2013.01); *A63B 2024/0065* (2013.01); *A63B 2024/0068* (2013.01)

(58) Field of Classification Search
CPC ....... A61B 5/1118; A61B 5/6824; A61B 5/02; A61B 5/021; A63B 2024/0065; A63B 2024/0068; A63B 2024/0071; A63B 24/0062

See application file for complete search history.

(56) References Cited

U.S. PATENT DOCUMENTS

| 2012/0326873 | A1 | 12/2012 | Utter |
| 2013/0184613 | A1 | 7/2013 | Homsi et al. |
| 2017/0239523 | A1 | 8/2017 | Cheng et al. |
| 2022/0117381 | A1 | 4/2022 | Li et al. |

OTHER PUBLICATIONS

International Search Report and Written Opinion for PCT Application No. PCT/US2021/036975, mailed Sep. 9, 2021, 10 pages.

*Primary Examiner* — Omkar A Deodhar
(74) *Attorney, Agent, or Firm* — Eversheds Sutherland (US) LLP

(57) ABSTRACT

Devices, systems, and methods are provided for performing volume and intensity-based activity evaluations. A method may include determining, by a device, a heart rate. The method may include determining, based on the heart rate, a motion threshold amount for a time period. The method may include determining motion data. The method may include comparing the motion data to the motion threshold for the time period. The method may include determining, based on the comparison of the motion data to the motion threshold for the time period, an activity intensity level associated with the heart rate and the motion data. The method may include determining, based on the activity intensity level, an activity score. The method may include sending data indicating the activity score for presentation at a second device.

20 Claims, 8 Drawing Sheets

VOLUME AND INTENSITY-BASED ACTIVITY EVALUATIONS FOR DEVICES

CROSS-REFERENCE TO RELATED PATENT APPLICATION(S)

This application is a continuation of U.S. Non-Provisional application Ser. No. 16/899,464, filed Jun. 11, 2020, the disclosure of which is incorporated by reference as set forth in full.

BACKGROUND

People increasingly are monitoring their activities and consumption habits to improve their health. Some activities that people may monitor include exercise, rest, and sedentary periods. People may be interested in the amount of time that they spend performing certain activities. However, some activity tracking methods using devices do not account for the intensity of an activity and a relationship between activity volume and activity intensity. Therefore, people may benefit from an enhanced activity evaluation using devices.

Figure 1:
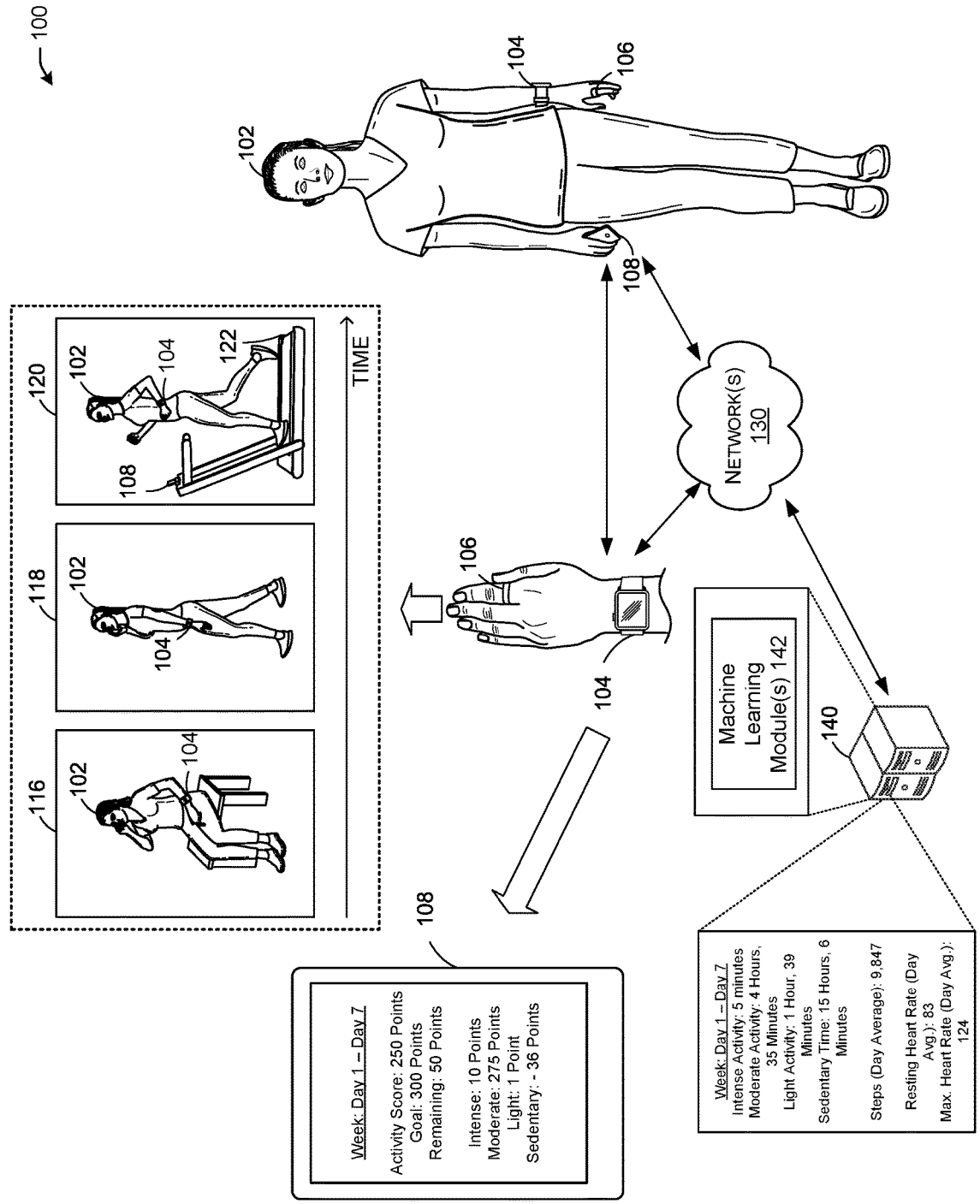
FIG. 1 illustrates an example system for volume and intensity-based activity evaluations using devices, in accordance with one or more example embodiments of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Overview

Example embodiments described herein provide certain systems, methods, and devices for performing volume and intensity-based activity evaluations.

A person's activities may be evaluated in a variety of ways. For example, user device data, such accelerometer or other motion and/or location data, may provide an indication of a person's activity intensity levels (e.g., whether the person with the user device moved a certain amount during a time period). Biometric data, such as heart rate (HR), breathing rate, pulse oximetry, and the like, may indicate whether a person is sleeping, sedentary, or active. The combination of device and biometric data may provide indications of activity intensity levels of a person over a period of time, such as a day or a week. Some activity monitoring techniques may not combine device and biometric data for activity analysis.

Not all activity may be the same and contribute the same amount to a person's health. For example, an hour of light exercise may provide a different level of physical benefit than an hour of intense exercise. In this manner, activity time may provide an indication of how active a person may be, and the intensity of activity may provide additional insight.

Thresholds may be used to measure levels of activity. For example, activity exceeding a threshold amount (e.g., a number of steps) may indicate how active a person has been, and a change in HR or breathing rate may indicate how active a person has been. In particular, more intense exercise for longer periods of time may correspond to more activity than less intense exercises for the same period of time or intense exercises for shorter periods of time. The thresholds used by some activity measuring techniques may not account for specific information about a particular person or the person's environment, such as the time of day, demographic information (e.g., the person's age), the person's health, the person's fitness level, and other factors.

The tracking and presentation of a user's activity may help a user monitor his or her health, and to track activity goals. Some activity measuring techniques may not track multiple types of activity over the course of multiple days, and may not provide an activity evaluation that allows a person to consider different amounts of different activities over the course of multiple days to reach activity goals.

Therefore, people may benefit from an enhanced method of determining and presenting a person's activity intensity levels using volume and intensity-based activity evaluations.

In one or more embodiments, activity scores may account for different amounts and types of activities. For example, an activity score may measure how active a person has been during a period of time, including a period of time that includes multiple days (e.g., week). The activity score may account for time when a person was stationary/sedentary, time when the person was active at a light intensity level, time when the person was active at a moderate intensity level, and time when the person was active at a high/vigorous intensity level. In this manner, rather than providing separate indications for how many steps a person walked or ran, how much time a person spent exercising, and how much time a person spent sedentary, a single activity score may account for each of those activities. For example, activity at higher intensity levels may be weighted higher than activity at lower intensity levels. Sedentary time may be subtracted from activity at light, moderate, and heavy activity intensity levels. Time asleep may be ignored to not subtract from activity at light, moderate, and heavy activity intensity levels.

In one or more embodiments, thresholds may be used to determine activity intensity levels. For example, a person's HR may be compared to threshold HRs. A person's amount of motion (e.g., a number of steps) may be compared to motion thresholds. A person's HR change (e.g., over a period of time) may be compared to HR change thresholds. Based on the amount of HR change over a time period, a device may determine whether a person was sedentary or was active at a light, moderate, or vigorous intensity level. To determine a person's HR change, a system may determine data from a prior time period (e.g., the three hours, or another amount of time, preceding the evaluated time period), and may filter out any non-stationary time. In this manner, the system may determine a person's stationary HR as a baseline for the HR change measurement.

In one or more embodiments, the thresholds used to determine activity intensity levels may depend on other data. Motion thresholds for a person at a first HR may be the same as or different from motion thresholds for a person at a second HR. HR change thresholds for a person at a first motion level may be different than HR change thresholds for a person at a second motion level. For example, when a person's HR for a period of time is below a first HR threshold, the person's motion data during the same period of time may be compared to one or more motion thresholds selected based on the HR being below the first HR threshold. When a person's HR for a period of time is above the first HR threshold, the person's motion data during the same period of time may be compared to one or more motion thresholds selected based on the HR being above the first HR threshold. For example, when a person's HR is high, the motion thresholds may be higher (e.g., 0-150 steps/min, >150 steps/min) than when the person's HR is lower (e.g., the motion thresholds may be 0-110 steps/min and >110 steps/min). In this manner, to achieve vigorous activity intensity, a person may not need to walk/run as many steps when the person's HR is lower than when the person's HR is higher. The HR change thresholds may be dependent on the motion thresholds. For example, a higher motion threshold (e.g., 150 steps/min) may require a smaller HR change than a lower motion threshold (e.g., 100 steps/min) in order to achieve vigorous intensity. In this manner, the intensity level may depend on a combination of HR and motion data, and the activity score based on the amount of time spent performing activity at the different intensities also may depend on the combination of HR and motion data. The activity score therefore may reflect the amount of activity at different intensities over a time period (e.g., a week), and the determination of activity intensities during the time period may be dynamic.

In one or more embodiments, the thresholds used to determine activity intensity levels may be dynamic based on information about a person. With user consent and in compliance with relevant laws, a user may opt into a system that determines and adjusts thresholds based on demographic data, such as a person's age, past activity intensity levels, health, fitness levels, and the like. In this manner, the amounts and levels of activity needed to reach a moderate or vigorous intensity for one person may be different than the amounts and levels of activity needed by another person. The activity score may be customizable for users rather than a "one size fits all" model.

In one or more embodiments, one or multiple devices may provide data used to determine a person's activity score. For example, devices may provide accelerometers or other motion data, and may provide biometric data. For example, one or multiple devices may detect HR data of a person, and the same device or another one or more devices may detect motion data. The HR and motion data may be collected by one of the devices for analysis, or may be sent to a remote network (e.g., a cloud-based computing network) for analysis. The device or system may collect the HR and motion data, may select a model (e.g., thresholds) based on a person's HR over a time period, may determine activity points for an activity score based on the model, and may add and/or subtract activity points over a time period to determine a person's overall activity score for the time period. The device or system may compare the person's overall activity score to an activity goal (e.g., a score threshold) to determine whether the person has achieved an activity goal during the time period, or how much additional activity (and at what intensities and durations) is needed to achieve the activity goal.

In one or more embodiments, the device or system that collects the HR and motion data and determines the person's activity score may present a person's real-time activity score in comparison to an activity goal, and/or may send such data to another device for presentation. In this manner, a person may be presented, on a device, with his/her activity score, whether the activity score has achieved an activity goal, how many activity points the person may need to achieve an activity goal, and/or suggested durations and intensities of activity for the person to achieve an activity goal.

The above descriptions are for purposes of illustration and are not meant to be limiting. Numerous other examples, configurations, processes, etc., may exist, some of which are described in greater detail below. Example embodiments will now be described with reference to the accompanying figures.

Illustrative Processes and Use Cases

FIG. 1 illustrates an example system 100 for volume and intensity-based activity evaluations using devices, in accordance with one or more example embodiments of the present disclosure.

Referring to FIG. 1, the system 100 may include a user 102 with multiple devices (e.g., device 104, device 106, device 108). For example, the user 102 may be wearing the device 104 (e.g., a wrist watch) and the device 106 (e.g., a ring device), and may be holding or carrying the device 108 (e.g., a smartphone). At step 116 (e.g., a time), the user 102 may be sedentary (e.g., sitting). At step 118 (e.g., a time), the user 102 may be walking (e.g., exercising lightly or moderately). At step 120, the user 102 may be jogging or running on a treadmill 122 (e.g., exercising moderately or vigorously). Step 116, step 118, and step 120 may represent different times throughout a day or multiple days (e.g., a week, month, etc.). The user 102 may be wearing or holding any one or more of the device 104, the device 106, and/or the device 108 at any of step 116, step 118, and step 120, or any one or more of the device 104, the device 106, and/or the device 108 may be otherwise monitoring, with user consent and consistent with appropriate laws, activity of the user 102 as explained further herein.

Still referring to FIG. 1, the system 100 may include one or more servers 140 (e.g., cloud-based servers remote from the device 104, the device 106, and/or the device 108), which may receive data from any one or more of the device 104, the device 106, and/or the device 108 (e.g., corresponding to step 116, step 118, and/or step 120). The data received by the one or more servers 140 from any one or more of the device 104, the device 106, and/or the device 108 may include biometric data and/or device data (e.g., accelerometer or other motion data captured by any one or more of the device 104, the device 106, and/or the device 108). The one or more servers 140 may analyze the biometric and/or device data to determine amounts of activity performed by the user 102 over a period of time (e.g., a week, a month, etc.). For example, the one or more servers 140 may determine quantities of intense activity, moderate activity, light activity, sedentary activity, and/or any other qualification or classification of activity intensity levels based on the biometric and/or device data of the user 102. The one or more servers 140 may determine the amount of time that the user 102 exercised at intense/vigorous, moderate, or light intensity activity levels, and the amount of time that the user 102 spent sedentary. The one or more servers 140 may determine the total and average number of steps (e.g., a daily or weekly total or average) that the user 102 performed over a time period. The one or more servers 140 may determine, using the biometric data, a resting HR and maximum HR (e.g., daily or weekly averages). The one or more servers 140 may include one or more machine learning (ML) modules 142 that may determine activity quantities and biometric levels, and may adjust the methods for such determinations (e.g., by adjusting activity and biometric thresholds) as the one or more ML modules 142 learn about the user 102. Alternatively, any of the device 104, the device 106, and/or the device 108 may collect the device and/or biometric data, and may perform the evaluations for activity intensity levels and biometric levels. The one or more servers 140 and/or any of the device 104, the device 106, and/or the device 108 may determine an activity score and provide activity information (e.g., including the activity score) to any of the device 104, the device 106, and/or the device 108 for presentation.

In one or more embodiments, activity scores may account for different amounts and types of activities. For example, an activity score may measure how active the user 102 has been during a period of time, including a period of time that includes multiple days (e.g., week). The activity score may account for time when the user 102 was stationary/sedentary (e.g., step 116), time when the person was active at a light intensity level (e.g., step 118), time when the person was active at a moderate intensity level (e.g., step 118 and/or step 120), and time when the person was active at a high/vigorous intensity level (e.g., step 120). In this manner, rather than providing separate indications for how many steps the user 102 walked or ran, how much time the user 102 spent exercising, and how much time the user 102 spent sedentary, a single activity score may account for each of those activities. For example, activity at higher intensity levels may be weighted higher than activity at lower intensity levels. Sedentary time may be subtracted from activity at light, moderate, and heavy intensity activity levels. Time asleep may be ignored to not subtract from activity at light, moderate, and heavy intensity activity levels.

In one or more embodiments, thresholds may be used to determine activity intensity levels. For example, the user's HR may be compared to threshold HRs. The user's amount of motion (e.g., a number of steps) may be compared to motion thresholds. The user's HR change (e.g., over a period of time) may be compared to HR change thresholds. Based on the amount of HR change over a time period, a device (e.g., the one or more servers 140 and/or any of the device 104, the device 106, and/or the device 108) may determine whether the user 102 was sedentary or was active at a light, moderate, or vigorous intensity level.

In one or more embodiments, the thresholds used to determine activity intensity levels may depend on other data. Motion thresholds for the user 102 at a first HR may be the same as or different from motion thresholds for the user 102 at a second HR. HR change thresholds for the user 102 at a first motion level may be different than HR change thresholds for the user 102 at a second motion level. For example, when the user's HR for a period of time is below a first HR threshold, the user's motion data during the same period of time may be compared to one or more motion thresholds selected based on the HR being below the first HR threshold. When the user's HR for a period of time is above the first HR threshold, the user's motion data during the same period of time may be compared to one or more motion thresholds selected based on the HR being above the first HR threshold. For example, when the user's HR is high, the motion thresholds may be higher (e.g., 0-150 steps/min, >150 steps/min) than when the user's HR is lower (e.g., the motion thresholds may be 0-110 steps/min and >110 steps/min). In this manner, to achieve vigorous activity intensity, the user 102 may not need to walk/run as many steps when the user's HR is lower than when the user's HR is higher. The HR change thresholds may be dependent on the motion thresholds. For example, a higher motion threshold (e.g., 150 steps/min) may require a smaller HR change than a lower motion threshold (e.g., 100 steps/min) in order to achieve vigorous intensity. In this manner, the intensity level may depend on a combination of HR and motion data, and the activity score based on the amount of time spent performing activity at the different intensities also may depend on the combination of HR and motion data. The activity score therefore may reflect the amount of activity at different intensities over a time period (e.g., a week), and the determination of activity intensities during the time period may be dynamic.

In one or more embodiments, the thresholds used to determine activity intensity levels may be dynamic based on information about the user 102. With user consent and in compliance with relevant laws, the user 102 may opt into a system that determines and adjusts thresholds based on demographic data, such as the user's age, past activity intensity levels, health, and the like.

In one or more embodiments, any of the device 104, the device 106, and/or the device 108 may provide (e.g., to any of the device 104, the device 106, and/or the device 108 and/or to the one or more servers 140) data used to determine the user's activity score. For example, any of the device 104, the device 106, and/or the device 108 may provide, to one another and/or to the one or more servers 140, accelerometer or other motion data, and may provide biometric data. For example, any of the device 104, the device 106, and/or the device 108 may detect HR data of the user 102, and the same device or another of the device 104, the device 106, and/or the device 108 may detect motion data. The HR and motion data may be collected by one of the devices and/or the one or more servers 140 for analysis. Any of the device 104, the device 106, and/or the device 108 or the one or more servers 140 may collect the HR and motion data, may select a model (e.g., thresholds) based on the user's HR over a time period, may determine activity points for an activity score based on the model, and may add and/or subtract activity points over a time period to determine the user's overall activity score for the time period. Any of the device 104, the device 106, and/or the device 108 or the one or more servers 140 may compare the user's overall activity score to an activity goal (e.g., a score threshold) to determine whether the user 102 has achieved an activity goal during the time period, or how much additional activity (and at what intensities and durations) is needed to achieve the activity goal.

In one or more embodiments, any of the device 104, the device 106, and/or the device 108 or the one or more servers 140 that collects the HR and motion data and determines the user's activity score may present the user's real-time activity score in comparison to an activity goal, and/or may send such data to any of the device 104, the device 106, and/or the device 108 for presentation. In this manner, user 102 may be presented, on a device, with his/her activity score, whether the activity score has achieved an activity goal, how many activity points the person may need to achieve an activity goal, and/or suggested durations and intensities of activity for the user 102 to achieve an activity goal. As shown in FIG. 1 as an example, the user's intense activity time may be five minutes; the user's moderate activity time may be four hours and thirty-five minutes; the user's light activity time may be one hour and thirty-nine minutes; the user's sedentary time may be fifteen hours and six minutes; the user's daily average of steps may be 9,847; the user's resting HR may be 83 (as a daily average); and the user's maximum HR may be 124 (as a daily average). As explained further herein, such data may result in an activity score of 250 for the time period (e.g., a week). Because a goal for the time period (e.g., as selected by the user 102 or predetermined by any of the device 104, the device 106, and/or the device 108 or the one or more servers 140) may be for the user 102 to achieve a score of 300 activity points for the time period, the remaining activity points may be 50 activity points. The activity score, the goal score, and the remaining points needed to reach the goal score from the activity score may be presented by any of the device 104, the device 106, and/or the device 108 along with the amount of points assigned to different intensity levels based on the amount of time spent at each activity intensity level or sedentary. For example, the five minutes of intense activity may result in 10 points; the four hours and thirty-five minutes of moderate activity may result in 275 points; the one hour and thirty-nine minutes of light activity may result in one point; and the fifteen hours and six minutes of sedentary time may result in negative thirty-six points. The activity score of 250 points may be the sum of the ten points, the 275 points, the 1 point, and the negative thirty-six points. In this manner, the activity score may account for multiple quantities of multiple levels of activity over time, the activity quantities and levels determined using a combination of device data and biometric data.

In one or more embodiments, the device 104, the device 106, the device 108, and/or the one or more servers 140 may include a personal computer (PC), a smart home device, a wearable wireless device (e.g., bracelet, watch, glasses, ring, etc.), a desktop computer, a mobile computer, a laptop computer, an Ultrabook™ computer, a notebook computer, a tablet computer, a server computer, a handheld computer, a handheld device, an internet of things (IoT) device, a sensor device, a PDA device, a handheld PDA device, an on-board device, an off-board device, a hybrid device (e.g., combining cellular phone functionalities with PDA device functionalities), a consumer device, a vehicular device, a non-vehicular device, a mobile or portable device, a non-mobile or non-portable device, a mobile phone, a cellular telephone, a PCS device, a PDA device which incorporates a wireless communication device, a mobile or portable GPS device, a DVB device, a relatively small computing device, a non-desktop computer, a "carry small live large" (CSLL) device, an ultra mobile device (UMD), an ultra mobile PC (UMPC), a mobile internet device (MID), an "origami" device or computing device, a device that supports dynamically composable computing (DCC), a context-aware device, a video device, an audio device, an A/V device, a set-top-box (STB), a Blu-ray disc (BD) player, a BD recorder, a digital video disc (DVD) player, a high definition (HD) DVD player, a DVD recorder, a HD DVD recorder, a personal video recorder (PVR), a broadcast HD receiver, a video source, an audio source, a video sink, an audio sink, a stereo tuner, a broadcast radio receiver, a flat panel display, a personal media player (PMP), a digital video camera (DVC), a digital audio player, a speaker, an audio receiver, an audio amplifier, a gaming device, a data source, a data sink, a digital still camera (DSC), a media player, a smartphone, a television, a music player, or the like. Other devices, including smart devices such as lamps, climate control, car components, household components, appliances, etc. may also be included in this list.

The device 104, the device 106, the device 108, and/or the one or more servers 140 may be configured to communicate via a communications network 130, wirelessly or wired (e.g., the same or different wireless communications networks). The communications network 130 may include, but not limited to, any one of a combination of different types of suitable communications networks such as, for example, broadcasting networks, cable networks, public networks (e.g., the Internet), private networks, wireless networks, cellular networks, or any other suitable private and/or public networks. Further, communications network 130 may have any suitable communication range associated therewith and may include, for example, global networks (e.g., the Internet), metropolitan area networks (MANs), wide area networks (WANs), local area networks (LANs), or personal area networks (PANs). In addition, communications network 130 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, white space communication mediums, ultra-high frequency communication mediums, satellite communication mediums, or any combination thereof.

Figure 2:
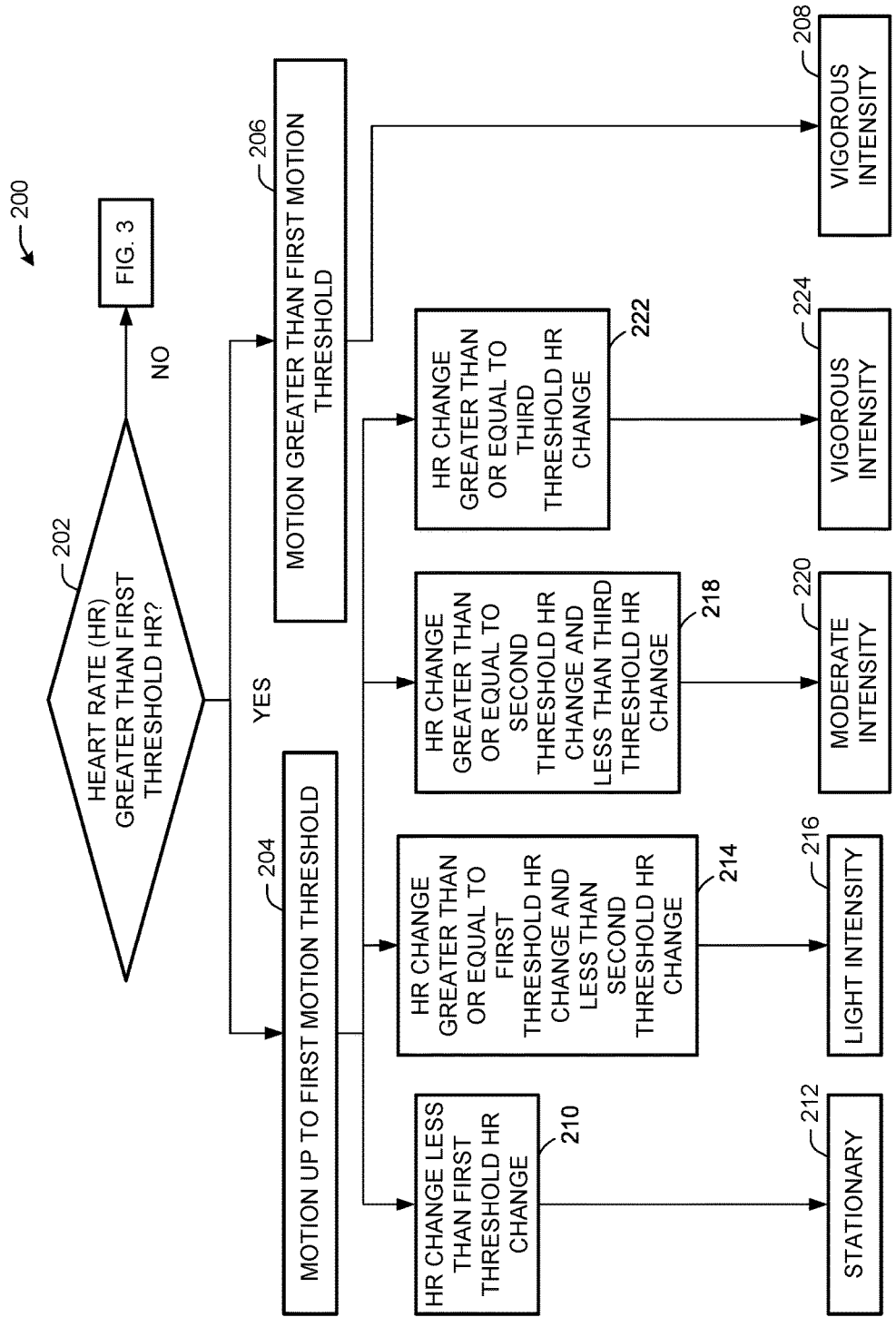
FIG. 2 illustrates an example flow diagram for performing volume and intensity-based activity evaluations, in accordance with one or more example embodiments of the present disclosure.

FIG. 2 illustrates an example flow diagram 200 for performing volume and intensity-based activity evaluations, in accordance with one or more example embodiments of the present disclosure.

Referring to FIG. 2, the flow diagram 200 illustrates determinations of levels of activity (e.g., performed by the user 102 of FIG. 1) based on biometric data and device (e.g., motion) data using a variety of thresholds. At block 202, a device (e.g., any of the device 104, the device 106, and/or the device 108 or the one or more servers 140 of FIG. 1 that collects HR and motion data for the user 102 of FIG. 1) may compare the user's HR to a first threshold HR. When the biometric data indicates that the person's HR is less than or equal to the first threshold HR, the process may continue at FIG. 3. When the biometric data indicates that the person's HR is greater than the first threshold HR, the process may continue at block 204 and/or block 206. When the device data indicates that the user's motion is up to (e.g., less than or equal to) a first motion threshold (the first motion threshold being based on the HR being greater than the first threshold HR) at block 204, the process may use one or more HR thresholds that are based on the motion being less than or equal to the first motion threshold. At block 206, when the device data indicates that the user's motion is greater than the first motion threshold, the process may proceed to block 208, where a determination may be made that the HR and motion data indicate that the time at which the HR data is greater than the first threshold HR and the motion data is greater than the first motion threshold indicates a vigorous intensity level (e.g., vigorous activity).

Still referring to FIG. 2, at block 210, when the HR data indicates (e.g., by comparing the user's HR at a first time to the user's HR at a second time) that the user's HR change (e.g., the difference in the user's HR at the first and second times) is less than a first threshold HR change (e.g., the first threshold HR change based on the motion being up to the first motion threshold and/or the HR being greater than the first threshold HR), the process may determine at block 212 that the HR and motion data indicate that the user was stationary at the time period when the HR was greater than the first threshold HR and when the motion is up to the first motion threshold. At block 214, when the HR data indicates (e.g., by comparing the user's HR at a first time to the user's HR at a second time) that the user's HR change is greater than or equal to the first threshold HR change and less than a second threshold HR change (e.g., the second threshold HR change based on the motion being up to the first motion threshold and/or the HR being greater than the first threshold HR), the process may determine at block 216 that the HR and motion data indicate that the user was exercising at a light intensity at the time period when the HR was greater than the first threshold HR and when the motion is up to the first motion threshold. At block 218, when the HR data indicates (e.g., by comparing the user's HR at a first time to the user's HR at a second time) that the user's HR change is greater than or equal to the second threshold HR change and less than a third threshold HR change (e.g., the third threshold HR change based on the motion being up to the first motion threshold and/or the HR being greater than the first threshold HR), the process may determine at block 220 that the HR and motion data indicate that the user was exercising at a moderate intensity at the time period when the HR was greater than the first threshold HR and when the motion is up to the first motion threshold. At block 222, when the HR data indicates (e.g., by comparing the user's HR at a first time to the user's HR at a second time) that the user's HR change is greater than or equal to the third threshold HR change, the process may determine at block 224 that the HR and motion data indicate that the user was exercising at a vigorous intensity at the time period when the HR was greater than the first threshold HR and when the motion is up to the first motion threshold.

Figure 3:
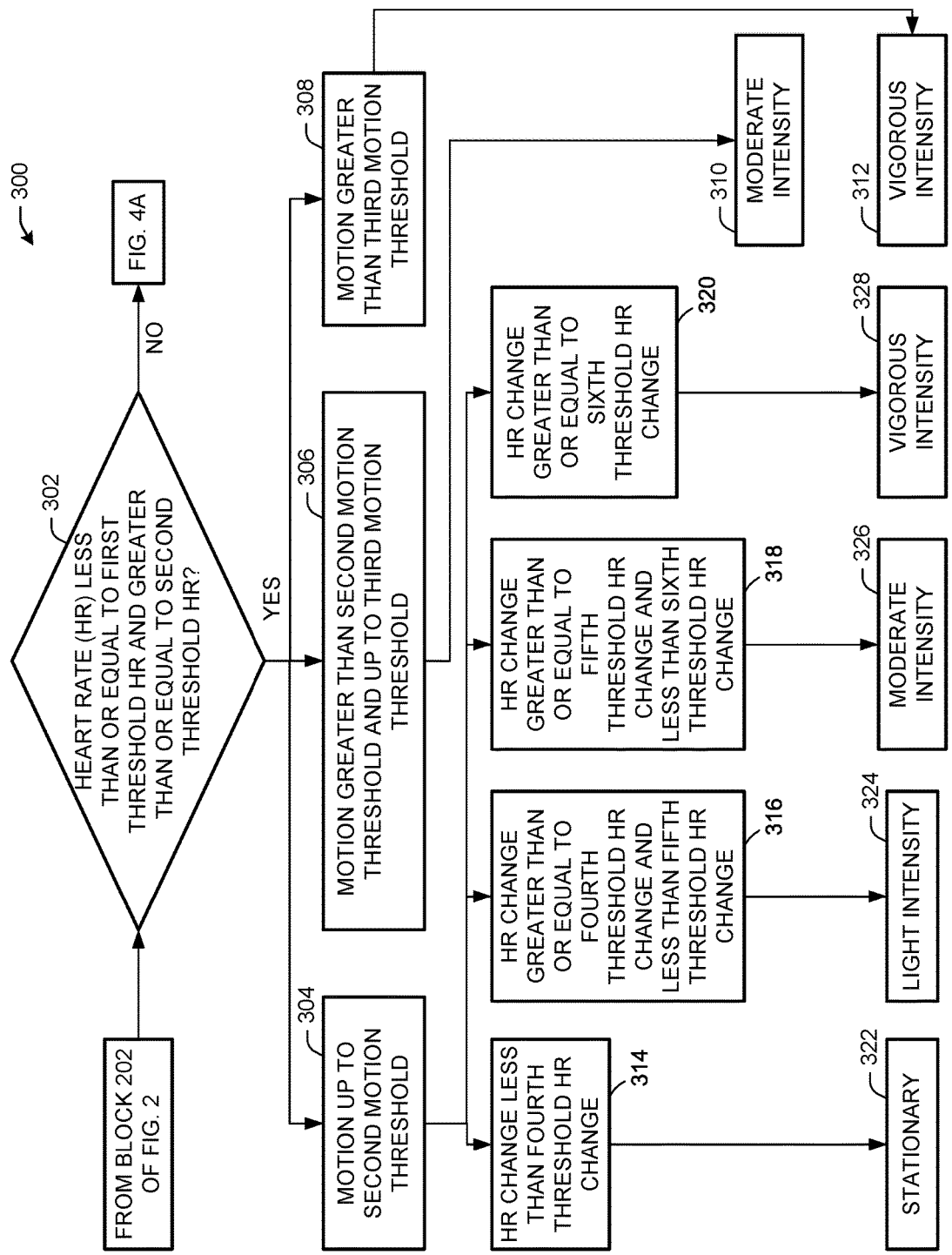
FIG. 3 illustrates an example flow diagram for performing volume and intensity-based activity evaluations, in accordance with one or more example embodiments of the present disclosure.

FIG. 3 illustrates an example flow diagram 300 for performing volume and intensity-based activity evaluations, in accordance with one or more example embodiments of the present disclosure.

Referring to FIG. 3, the flow diagram 300 illustrates determinations of levels of activity (e.g., performed by the user 102 of FIG. 1) based on biometric data and device (e.g., motion) data using a variety of thresholds. As noted with regard to FIG. 2, at block 202, a device (e.g., any of the device 104, the device 106, and/or the device 108 or the one or more servers 140 of FIG. 1 that collects HR and motion data for the user 102 of FIG. 1) may compare the user's HR to a first threshold HR. When the biometric data indicates that the person's HR is less than or equal to the first threshold HR, the process may continue at FIG. 3. At block 302, a device (e.g., any of the device 104, the device 106, and/or the device 108 or the one or more servers 140 of FIG. 1 that collects HR and motion data for the user 102 of FIG. 1) may compare the user's HR to the first threshold HR and to a second threshold HR. When the biometric data indicates that the person's HR is less than or equal to the first threshold HR and greater than or equal to a second threshold HR (e.g., within a range from the second threshold HR to the first threshold HR), the process may continue to block 304. When the biometric data indicates that the person's HR is less than the second threshold HR, the process may continue at FIG. 4A. When the biometric data indicates that the person's HR is in the range from the second threshold HR to the first threshold HR, the process may continue at block 304, block 306, and/or block 308. At block 304, when the device data indicates that the user's motion is up to (e.g., less than or equal to) a second motion threshold (the second motion threshold being based on the HR being in the range from the second threshold HR to the first threshold HR), the process may use one or more HR thresholds that are based on the motion being less than or equal to the second motion threshold. At block 306, when the device data indicates that the user's motion is greater than the second motion threshold and up to a third motion threshold (the third motion threshold being based on the HR being in the range from the second threshold HR to the first threshold HR), the process may use one or more HR thresholds that are based on the motion being greater than the second motion threshold and up to the third motion threshold. For example, the process may continue at block 310 where the HR data and device data indicate that the user's activity was performed at a moderate intensity. At block 308, when the device data indicates that the user's motion is greater than the third motion threshold, the process may proceed to block 312, where a determination may be made that the HR and motion data a vigorous intensity level (e.g., vigorous activity).

Still referring to FIG. 3, at block 314, when the HR data indicates (e.g., by comparing the user's HR at a first time to the user's HR at a second time) that the user's HR change (e.g., the difference in the user's HR at the first and second times) is less than a fourth threshold HR change (e.g., the fourth threshold HR change based on the motion being up to the second motion threshold and/or the HR being in the range from the second threshold HR to the first threshold HR), the process may determine at block 322 that the HR and motion data indicate that the user was stationary at the time period when the HR was in the range from the second threshold HR to the first threshold HR and when the motion is up to the second motion threshold. At block 316, when the HR data indicates (e.g., by comparing the user's HR at a first time to the user's HR at a second time) that the user's HR change is greater than or equal to the fourth threshold HR change and less than a fifth threshold HR change (e.g., the fifth threshold HR change based on the motion being up to the second motion threshold and/or the HR being in the range from the second threshold HR to the first threshold HR), the process may determine at block 324 that the HR and motion data indicate that the user was exercising at a light intensity at the time period when the HR was in the range from the second threshold HR and the first threshold HR, and when the motion is up to the second motion threshold. At block 318, when the HR data indicates (e.g., by comparing the user's HR at a first time to the user's HR at a second time) that the user's HR change is greater than or equal to the fifth threshold HR change and less than a sixth threshold HR change (e.g., the sixth threshold HR change based on the motion being up to the second motion threshold and/or the HR being in the range from the second threshold HR to the first threshold HR), the process may determine at block 326 that the HR and motion data indicate that the user was exercising at a moderate intensity. At block 320, when the HR data indicates (e.g., by comparing the user's HR at a first time to the user's HR at a second time) that the user's HR change is greater than or equal to the sixth threshold HR change, the process may determine at block 328 that the HR and motion data indicate that the user was exercising at a vigorous intensity.

Figure 4A:
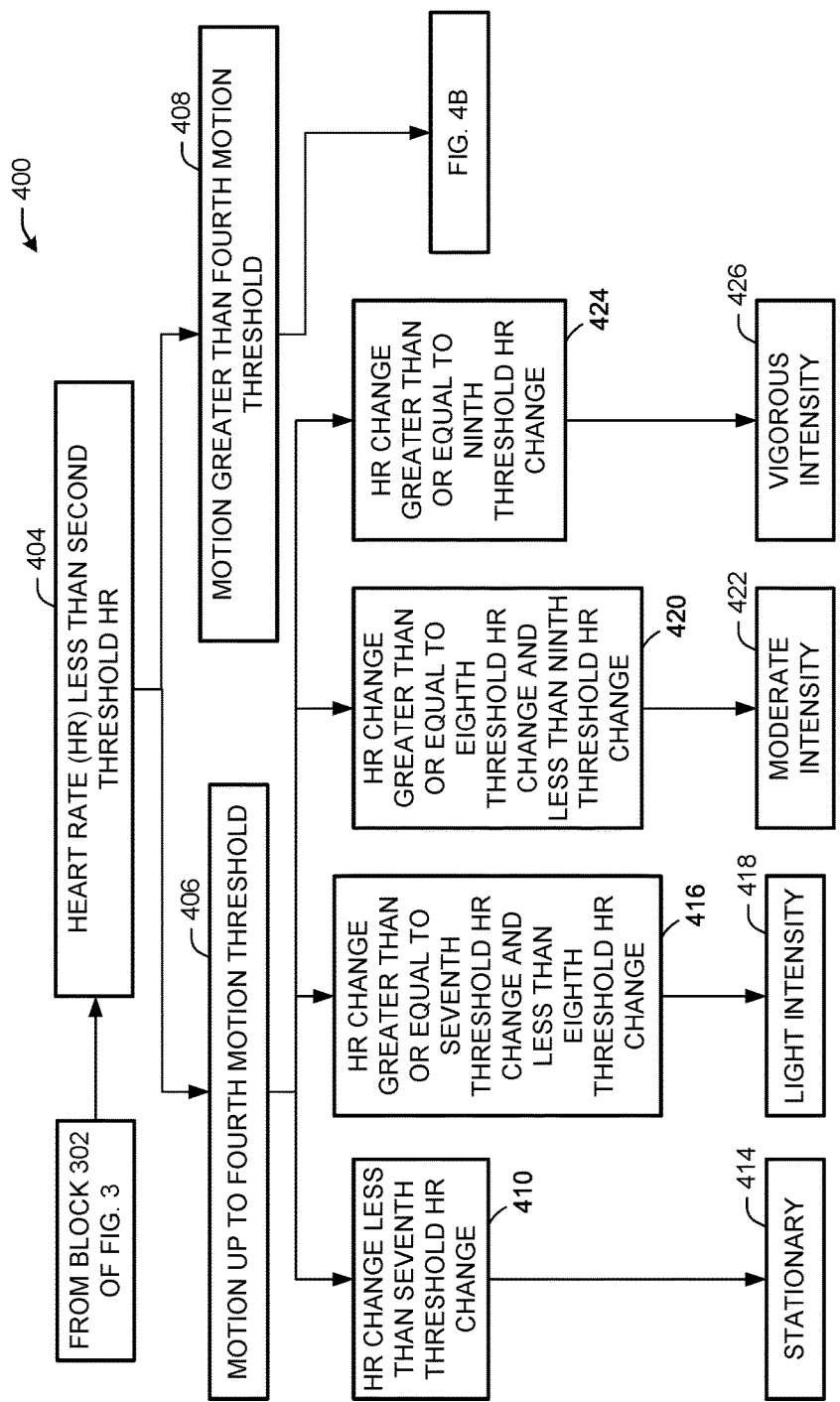
FIG. 4A illustrates an example flow diagram for performing volume and intensity-based activity evaluations, in accordance with one or more example embodiments of the present disclosure.

FIG. 4A illustrates an example flow diagram 400 for performing volume and intensity-based activity evaluations, in accordance with one or more example embodiments of the present disclosure.

Referring to FIG. 4A, the flow diagram 400 illustrates determinations of levels of activity (e.g., performed by the user 102 of FIG. 1) based on biometric data and device (e.g., motion) data using a variety of thresholds. As noted with regard to FIG. 3, at block 302, a device (e.g., any of the device 104, the device 106, and/or the device 108 or the one or more servers 140 of FIG. 1 that collects HR and motion data for the user 102 of FIG. 1) may compare the user's HR to a first threshold HR and a second threshold. When the biometric data indicates that the person's HR is in the range from the first threshold HR to the first threshold HR, the process may continue at FIG. 4A. At block 402, a device (e.g., any of the device 104, the device 106, and/or the device 108 or the one or more servers 140 of FIG. 1 that collects HR and motion data for the user 102 of FIG. 1) may compare the user's HR to the second threshold HR. When the biometric data indicates that the person's HR is less than the second threshold HR, the process may continue to block 406 and/or block 408. At block 406, when the device data indicates that the user's motion is up to (e.g., less than or equal to) a fourth motion threshold (the fourth motion threshold being based on the HR being less than the second threshold HR), the process may use one or more HR thresholds that are based on the motion being less than or equal to the fourth motion threshold. At block 408, when the device data indicates that the user's motion is greater than the fourth motion threshold, the process may use one or more HR thresholds that are based on the motion being greater than the fourth motion threshold. For example, the process may continue to FIG. 4B.

Still referring to FIG. 4A, at block 410, when the HR data indicates (e.g., by comparing the user's HR at a first time to the user's HR at a second time) that the user's HR change (e.g., the difference in the user's HR at the first and second times) is less than a seventh threshold HR change (e.g., the seventh threshold HR change based on the motion being up to the fourth motion threshold and/or the HR being less than the second threshold HR), the process may determine at block 414 that the HR and motion data indicate that the user was stationary. At block 416, when the HR data indicates (e.g., by comparing the user's HR at a first time to the user's HR at a second time) that the user's HR change is greater than or equal to the seventh threshold HR change and less than an eighth threshold HR change (e.g., the eighth threshold HR change based on the motion being up to the fourth motion threshold and/or the HR being less than the second threshold HR), the process may determine at block 418 that the HR and motion data indicate that the user was exercising at a light intensity. At block 420, when the HR data indicates (e.g., by comparing the user's HR at a first time to the user's HR at a second time) that the user's HR change is greater than or equal to the eighth threshold HR change and less than a ninth threshold HR change (e.g., the ninth threshold HR change based on the motion being up to the fourth motion threshold and/or the HR being less than the second threshold HR), the process may determine at block 422 that the HR and motion data indicate that the user was exercising at a moderate intensity. At block 424, when the HR data indicates (e.g., by comparing the user's HR at a first time to the user's HR at a second time) that the user's HR change is greater than or equal to the ninth threshold HR change, the process may determine at block 426 that the HR and motion data indicate that the user was exercising at a vigorous intensity.

Figure 4B:
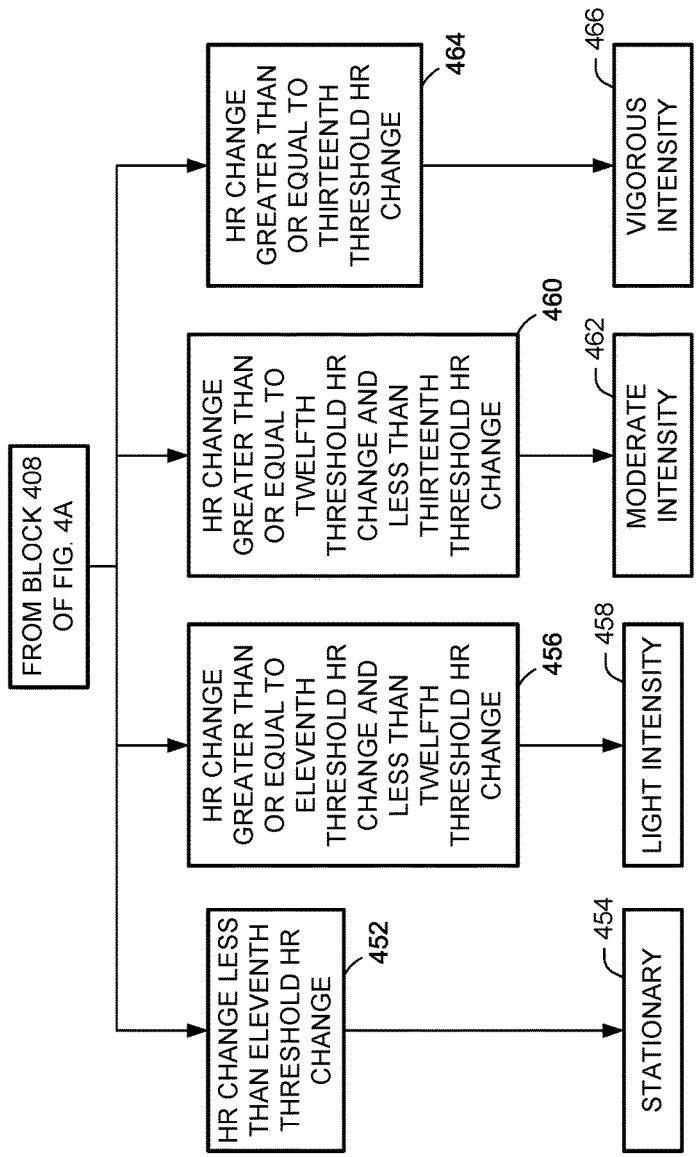
FIG. 4B illustrates an example flow diagram for performing volume and intensity-based activity evaluations, in accordance with one or more example embodiments of the present disclosure.

FIG. 4B illustrates an example flow diagram 450 for performing volume and intensity-based activity evaluations, in accordance with one or more example embodiments of the present disclosure.

Referring to FIG. 4B, the flow diagram 450 illustrates determinations of levels of activity (e.g., performed by the user 102 of FIG. 1) based on biometric data and device (e.g., motion) data using a variety of thresholds. As noted with regard to FIG. 4A, at block 408, a device (e.g., any of the device 104, the device 106, and/or the device 108 or the one or more servers 140 of FIG. 1 that collects HR and motion data for the user 102 of FIG. 1) may determine that the motion data indicate that the user's motion exceeds the fourth motion threshold. Based on the user's HR being less than the second threshold HR and the motion exceeding the fourth motion threshold, one or more threshold HR changes may be used to determine activity intensity levels.

Still referring to FIG. 4B, at block 452 when the HR data indicates that the HR change is less than an eleventh threshold HR change (e.g., the eleventh threshold HR change being based on the HR being less than the second threshold HR and/or the motion being greater than the fourth motion threshold), the process may continue to block 454 where the evaluating device (e.g., any of the device 104, the device 106, and/or the device 108 or the one or more servers 140 of FIG. 1 that collects HR and motion data for the user 102 of FIG. 1) may determine that the biometric and device data indicate that the user was stationary. At block 456 when the HR data indicates that the HR change is greater than or equal to the eleventh threshold and less than a twelfth threshold HR change (e.g., the twelfth threshold HR change being based on the HR being less than the second threshold HR and/or the motion being greater than the fourth motion threshold), the process may continue to block 458 where the evaluating device (e.g., any of the device 104, the device 106, and/or the device 108 or the one or more servers 140 of FIG. 1 that collects HR and motion data for the user 102 of FIG. 1) may determine that the biometric and device data indicate that the user was exercising at a light intensity level. At block 464 when the HR data indicates that the HR change is greater than or equal to the thirteenth threshold HR change, the process may continue to block 466 where the evaluating device (e.g., any of the device 104, the device 106, and/or the device 108 or the one or more servers 140 of FIG. 1 that collects HR and motion data for the user 102 of FIG. 1) may determine that the biometric and device data indicate that the user was exercising at a vigorous intensity level.

Referring to FIGS. 2-4B, a device (e.g., any of the device 104, the device 106, and/or the device 108 or the one or more servers 140 of FIG. 1 that collects HR and motion data for the user 102 of FIG. 1) may determine an activity score based on the amounts of time that the user was sedentary and/or exercised at the different activity intensity levels (e.g., as explained above with regard to FIG. 1). At any time during a time period (e.g., during the course of a week), the user's biometric and device data may be compared to the various thresholds to determine whether, at a given time, the user was sedentary or exercising at any intensity level. The amount of activity points assigned for sedentary periods and periods when the user was exercising at any intensity level may vary. For example, an increment of time when the user was sedentary may be multiplied by zero or a negative number; an increment of time when the user exercised at light intensity may be multiplied by a first positive number; an increment of time when the user exercised at moderate intensity may be multiplied by a second positive number (e.g., greater than the first positive number for light intensity); and an increment of time when the user exercised at a vigorous intensity may be multiplied by a third positive number (e.g., greater than the second positive number for moderate intensity). For example, the increment of time may be a second, a minute, multiple seconds or minutes, hours, or the like. Each increment of time sedentary or at any exercise intensity level may be multiplied by the negative, zero, and/or positive numbers and added together to result in an activity score. In this manner, the user's activity score may update over time (e.g., during the course of a week), and may be compared to a goal for a time period. When the activity score is less than the goal, the device may determine the number of activity points needed to reach the goal from the current activity score (e.g., the difference between the activity score and the goal), the average number of activity points needed to reach the goal, and/or the average number of increments of time needed at one or more intensity levels to result in sufficient activity points to reach the goal. The device may present the score information or may send the score information to another device for presentation.

Still referring to FIGS. 2-4B, the thresholds may be dynamic not only with respect to one another, but may vary based on the time of day, the day of the week, and/or user data (e.g., user age, health, previous activity intensity levels, and the like). Any of the motion thresholds may be the same as or different than a motion threshold for a HR range (e.g., a motion threshold in FIG. 3. FIG. 4A, and/or FIG. 4B may be the same as or different than a motion threshold of FIG. 2, and so on). In this manner, for different HR ranges, motion ranges based on the thresholds may be the same and/or may vary, and may overlap a threshold for any HR threshold. For example, when the user's HR satisfies the range of block 302 of FIG. 3, the motion range of block 306 may overlap a motion range from the first motion threshold of block 204 to the second motion threshold of block 206 of FIG. 2, and so on. Any of the threshold HR changes may be the same as or different than a threshold HR change for a HR range (e.g., a threshold HR change in FIG. 3, FIG. 4A, and/or FIG. 4B may be the same as or different than a threshold HR change of FIG. 2, and so on). In this manner, for different HR ranges, HR change ranges based on the thresholds may be the same and/or may vary, and may overlap a threshold for any HR threshold. For example, when the user's motion satisfies the range of block 306 of FIG. 3, the HR change range of block 316 may overlap a HR change range from the first threshold HR change of block 210 to the second threshold HR change of block 216 of FIG. 2, and so on.

Still referring to FIGS. 2-4B, any number of thresholds may be used. For example, a person's HR may be compared to multiple HR ranges established by multiple HR thresholds. Any HR range may have one or more multiple motion thresholds. While FIG. 3 shows three motion thresholds, for example, more than three motion thresholds may correspond to a HR or HR range. The numbers and combinations of thresholds shown in FIGS. 2-4B are examples, and are not meant to be limiting.

Still referring to FIGS. 2-4B, to determine a person's HR change, a system may determine data from a prior time period (e.g., the three hours, or another amount of time, preceding the evaluated time period), and may filter out any non-stationary time. In this manner, the system may determine a person's stationary HR as a baseline for the HR change measurement.

Figure 5A:
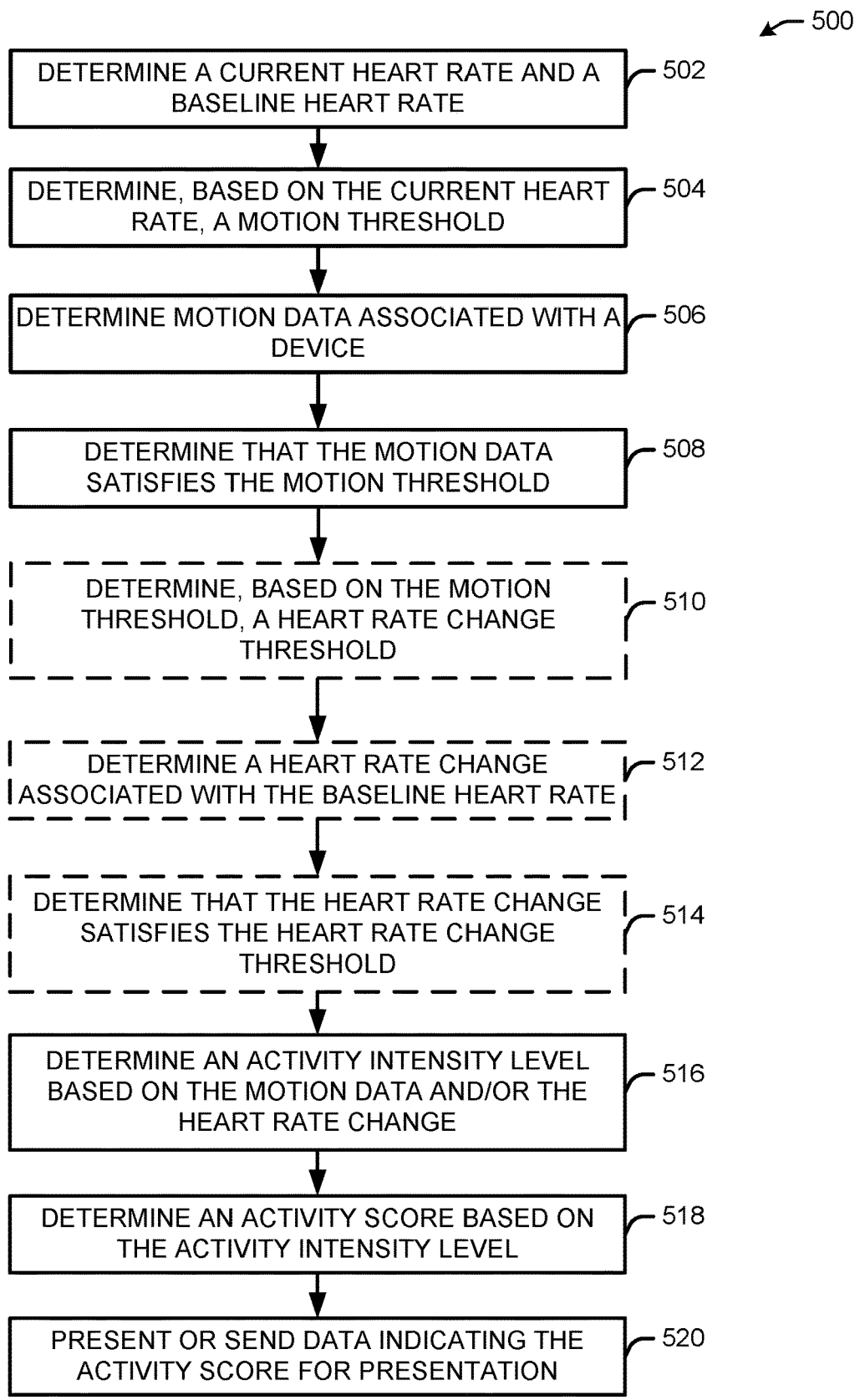
FIG. 5A illustrates a flow diagram for a process for performing volume and intensity-based activity evaluations, in accordance with one or more example embodiments of the present disclosure.

FIG. 5A illustrates a flow diagram for a process 500 for performing volume and intensity-based activity evaluations, in accordance with one or more example embodiments of the present disclosure.

At block 502, a device (e.g., the device 104 of FIG. 1, the device 106 of FIG. 1, the device 108 of FIG. 1, the one or more servers 140 of FIG. 1) may determine a current heart rate (HR) of a person (e.g., the user 102 of FIG. 1) and a baseline HR of the person. The device may receive biometric sensor data, detected by a sensor of the device or received from another device, that indicates the person's HR at a time or during a period of time (e.g., from one time to a second time). For example, the HR may be a value measured in beats per minute (bpm). The device may compare the HR to one or more threshold HRs (e.g., block 202 of FIG. 2, block 302 of FIG. 3, block 404 of FIG. 4A). The one or more threshold HRs may be based on one or more criteria, such as the person's age, the person's health, the time of day or day of the week, past exercise data of the person, and the like. For example, a threshold HR may be a maximum age-predicted heart rate (MPHR). In this manner, the threshold HRs and their corresponding HR ranges in block 202 of FIG. 2, block 302 of FIG. 3, and/or block 404 of FIG. 4A may be threshold MPHR values. The baseline HR may be based on data from a prior time period (e.g., the three hours, or another amount of time, preceding the evaluated time period). The device may filter out any non-stationary time from the prior HR data. In this manner, the device may determine a person's stationary HR as a baseline.

At block 504, the device may determine, based on the current HR of block 502, a motion threshold. As shown in FIG. 2-FIG. 4B, motion thresholds may depend on the threshold HR. For example, when the HR of block 502 is greater than 75% of a MPHR, one or more motion thresholds used to determine whether the HR is indicative of an activity intensity level or that the person was sedentary may be different than the motion thresholds used to determine whether the HR is indicative of an activity intensity level or that the person was sedentary when the HR of block 502 is less than 75% of the MPHR. In this manner, the amount of motion (e.g., indicated by device data) to achieve vigorous intensity exercise may be different when a person's HR is higher than when the person's HR is lower.

At block 506, the device may determine motion data. The motion data may include device data detected by the device (e.g., using an accelerometer, magnetometer, etc.) and/or device data received by another device. The motion data may indicate how active the person was at a given time or during a period of time. For example, when the device is wearable and/or receives motion data from a wearable device, the motion data may be an indication of movement of the person, such as the number of steps that the person took during a time period (e.g., minutes, hours, days, etc.).

At block 508, the device may determine that the motion data satisfies the motion threshold of block 506. Satisfying the motion threshold may refer to determining which motion threshold or thresholds of one or more motion thresholds are met by the motion data. Block 204 of FIG. 2, block 206 of FIG. 2, block 304 of FIG. 3, block 306 of FIG. 3, block 308 of FIG. 3, block 406 of FIG. 4A, and block 408 of FIG. 4A show examples of comparing the motion data to various motion thresholds to determine a motion range satisfied by the motion data. For example, when there is only one motion threshold, satisfying the motion threshold may refer to the motion data being above or below the threshold (or at the threshold). Threshold HR changes for when the motion data is below a motion threshold may be different than threshold HR changes for when the motion data is above the motion threshold. When there are multiple motion thresholds, satisfying a motion threshold may refer to being within a motion range (e.g., zero to a first motion threshold, between a first motion threshold and a second motion threshold, greater than the second motion threshold, etc.).

At block 510, the device may determine, based on the motion threshold, a threshold HR change. As explained above at block 508, threshold HR changes for when the motion data is below a motion threshold may be different than threshold HR changes for when the motion data is above the motion threshold. Threshold HR change may be different based on the HR of block 502 as well. In this manner, the threshold HR changes of block 210, block 214, block 218, and block 222 of FIG. 2 may differ from the threshold HR changes of block 314, block 316, block 318, and block 320 of FIG. 3, for example. At a higher HR, the HR change (as indicated by change of HR of block 502 from one time to a later time) threshold indicating exercise at a vigorous intensity may be different than the HR change threshold for a lower HR. In this manner, motion and HR thresholds may vary based on one another and/or based on user data, environmental data, and the like. During the course of multiple days, for example, the thresholds at different times may vary, so the levels of activity for a person may be determined based on varying criteria during the evaluated time period.

At block 512, the device may determine a HR change associated with the baseline HR of block 502. For example, the device may use the HR data of block 502 to determine that a person's HR changed from HR1 at time t1 to HR2 at time t2. The HR change may be represented by the difference of HR2-HR1. The HR change may be a measurement of bpm, or may be a percentage of MPHR (e.g., HR2-HR1 may indicate HR2's percentage of a MPHR-HR1's percentage of the MPRH).

At block 514, the device may determine that the HR change satisfies the threshold HR change of block 510. Satisfying the threshold HR change may refer to determining which threshold HR change or HR change thresholds of one or more HR change thresholds are met by the HR data. Block 210 of FIG. 2, block 214 of FIG. 2, block 218 of FIG. 2, block 222 of FIG. 2, block 314 of FIG. 3, block 316 of FIG. 3, block 318 of FIG. 3, block 320 of FIG. 3, block 410 of FIG. 4A, block 416 of FIG. 4A, block 420 of FIG. 4A, block 424 of FIG. 4A, block 452 of FIG. 4B, block 456 of FIG. 4B, block 460 of FIG. 4B, and block 464 of FIG. 4B show examples of comparing the HR change data to various HR change thresholds to determine a range of HR changes satisfied by the HR change data. For example, when there is only one threshold HR change, satisfying the threshold HR change may refer to the HR change data being above or below the threshold (or at the threshold). When there are multiple HR change thresholds, satisfying a threshold HR change may refer to being within a range of HR change thresholds (e.g., zero to a first HR change threshold, between a first HR change threshold and a second HR change threshold, greater than the second HR change threshold, etc.).

At block 516, the device may determine an activity intensity level based on the HR change and/or the motion data. For example, the HR change and the HR change threshold of block 510, block 512, and block 514 may be optional because the motion data satisfying a motion threshold may indicate an activity intensity level without considering a HR change. Block 208 of FIG. 2, block 310 of FIG. 3, and block 312 of FIG. 3 are examples of when the satisfaction of a motion threshold corresponds to an activity intensity level regardless of a person's HR change. Block 212 of FIG. 2, block 216 of FIG. 2, block 220 of FIG. 2, block 224 of FIG. 2, block 314 of FIG. 3, block 316 of FIG. 3, block 318 of FIG. 3, block 320 of FIG. 3, block 414 of FIG. 4A, block 418 of FIG. 4A, block 422 of FIG. 4A, block 426 of FIG. 4A, block 454 of FIG. 4B, block 458 of FIG. 4B, block 462 of FIG. 4B, and block 466 of FIG. 4B show examples of an activity intensity level being indicated by the satisfaction of one or more motion thresholds and one or more HR change thresholds. Activity intensity levels may include sedentary/stationary intensity, light intensity activity, moderate intensity activity, vigorous/high intensity activity, and the like.

At block 518, the device may determine an activity score based on the activity intensity level. The device may determine an activity score based on the amounts of time that the user was sedentary and/or exercised at the different activity intensity levels (e.g., as explained above with regard to FIG. 1). The amount of activity points assigned for sedentary periods and periods when the user was exercising at any intensity level may vary. For example, an increment of time when the user was sedentary may be multiplied by zero or a negative number; an increment of time when the user exercised at light intensity may be multiplied by a first positive number; an increment of time when the user exercised at moderate intensity may be multiplied by a second positive number (e.g., greater than the first positive number for light intensity); and an increment of time when the user exercised at a vigorous intensity may be multiplied by a third positive number (e.g., greater than the second positive number for moderate intensity). For example, the increment of time may be a second, a minute, multiple seconds or minutes, hours, or the like. Each increment of time sedentary or at any exercise intensity level may be multiplied by the negative, zero, and/or positive numbers and added together to result in an activity score. In this manner, the user's activity score may update over time (e.g., during the course of a week), and may be compared to a goal for a time period. Motion and HR measurements may be taken in time increments (e.g., every thirty seconds). In this manner, the activity score may represent a block of time including multiple increments at which motion and HR are measured. For example, five minutes of activity at an activity intensity level may include ten measurements of HR and motion that indicate that the user was active at an intensity level for the five minute duration.

At block 520, the device may present data indicating the activity score or may send data indicating the activity score to another device for presentation. For example, the presentation data may appear as shown in FIG. 1. When the activity score is less than a goal (e.g., a goal activity score for a period of time), the device may determine the number of activity points needed to reach the goal from the current activity score (e.g., the difference between the activity score and the goal), the average number of activity points needed to reach the goal, and/or the average number of increments of time needed at one or more intensity levels to result in sufficient activity points to reach the goal. The device may present the score information or may send the score information to another device for presentation. The activity score may be for an entire duration (e.g., for a week of activity), or may indicate whether a person is on pace for the duration (e.g., whether the person scored enough activity points in a respective day to be on pace to reach a weekly goal). In this manner, the activity score data may provide real-time update to the user to provide incremental goals and feedback that may allow a user to achieve an activity goal.

Figure 5B:
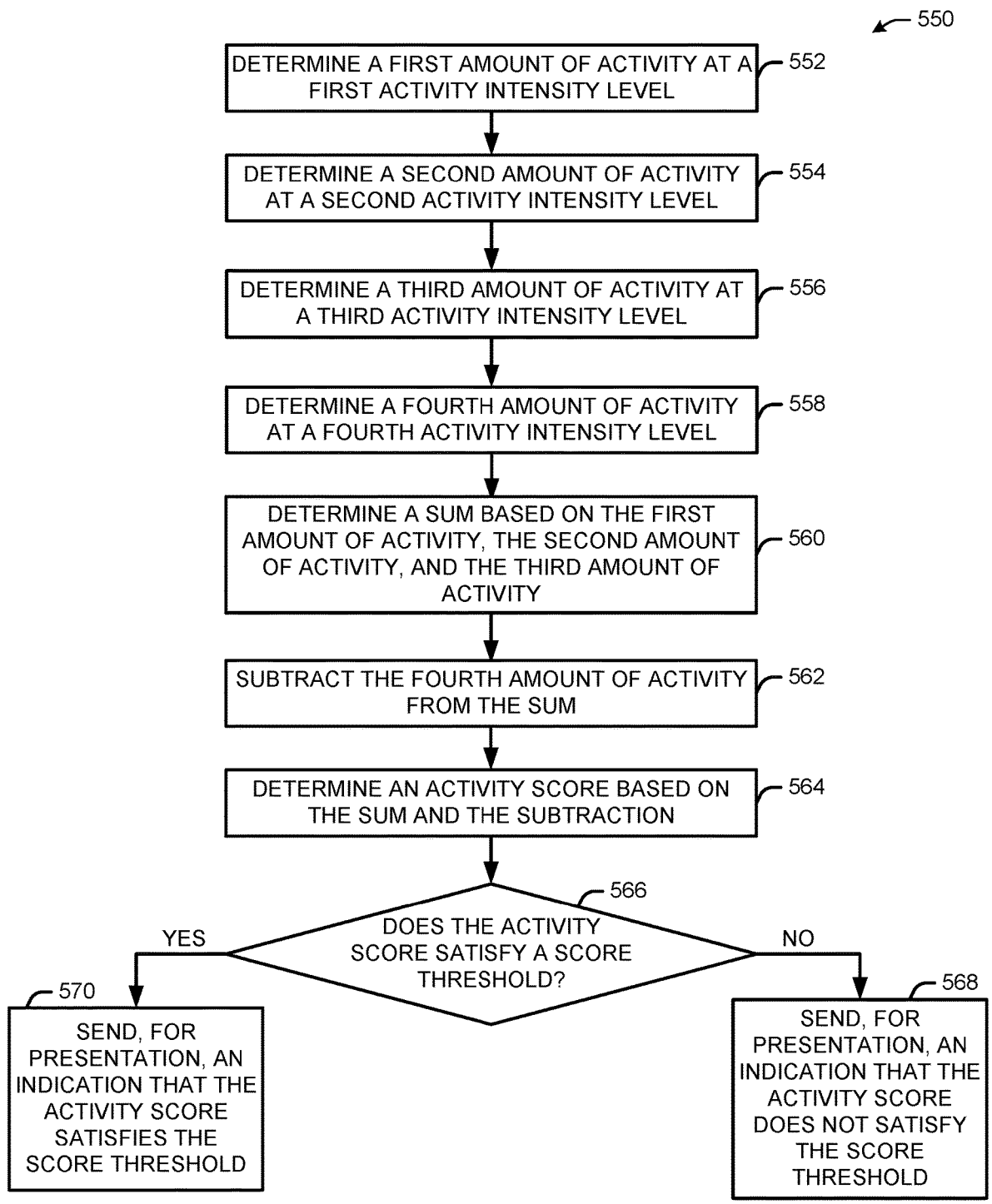
FIG. 5B illustrates a flow diagram for a process for performing volume and intensity-based activity evaluations, in accordance with one or more example embodiments of the present disclosure.

FIG. 5B illustrates a flow diagram for a process 550 for performing volume and intensity-based activity evaluations, in accordance with one or more example embodiments of the present disclosure.

At block 552, a device (e.g., the device 104 of FIG. 1, the device 106 of FIG. 1, the device 108 of FIG. 1, the one or more servers 140 of FIG. 1) may determine a first amount of activity at a first activity intensity level. At block 554, the device may determine a second amount of activity at a second activity intensity level. At block 556 the device may determine a third amount of activity at a third activity intensity level. At block 558 the device may determine a fourth amount of activity at a fourth activity intensity level. For example, the first, second, and third activity intensity levels may be light intensity, moderate intensity, or vigorous/high intensity (e.g., as determined using FIG. 2, FIG. 3, FIG. 4A, and/or FIG. 4B). The fourth activity intensity level may indicate that a person (e.g., the user 102 of FIG. 1) was sedentary/stationary (e.g., as determined using FIG. 2, FIG. 3, FIG. 4A, and/or FIG. 4B). Motion and HR measurements used to determine activity intensity levels may be taken in time increments (e.g., every thirty seconds). In this manner, the activity intensity levels may represent a block of time including multiple increments at which motion and HR are measured. For example, five minutes of activity at an activity intensity level may include ten measurements of HR and motion that indicate that the user was active at an intensity level for the five minute duration.

The activity intensity levels of block 552, block 554, block 556, and block 558 may correspond to the person's biometric data and device data (e.g., accelerometer data indicated by the device and/or another device) at multiple times. In this manner, the device may determine activity scores based on the biometric and device data at different times over the course of a time period (e.g., a week). For example, the first amount of activity at the first activity intensity level may correspond to an amount of time when the person's biometric data and device data indicates that the person was exercising at the first activity intensity level. The second amount of activity at the second activity intensity level may correspond to an amount of time when the person's biometric data and device data indicates that the person was exercising at the second activity intensity level. The third amount of activity at the third activity intensity level may correspond to an amount of time when the person's biometric data and device data indicates that the person was exercising at the third activity intensity level. The fourth amount of activity at the fourth activity intensity level may correspond to an amount of time when the person's biometric data and device data indicates that the person was sedentary. The amounts (e.g., the amounts of time) for an activity intensity level may vary. For example, the first amount may indicate that a person was walking for sixty minutes. The second amount may indicate that a person was jogging for thirty minutes. The third amount may indicate that a person was running for fifteen minutes. Any of the activity intensity levels may be the same (e.g., multiple of the first, second, and third activity intensity levels may indicate moderate activity, and the respective amounts may represent different times when the person was active at a moderate intensity activity level).

At block 560, the device may determine a sum of the amounts of non-sedentary activity levels. For example, when the first, second, and third activity intensity levels of block 552, block 554, and block 556 indicate non-sedentary activity levels (e.g., light activity, moderate activity, and/or vigorous/high activity), the amounts of time or the activity points corresponding to the amounts of time may be added together over a duration. For example, all of the non-sedentary activity over the course of multiple days or a week may be summed. The amounts of time that a person was not sleeping and/or sedentary during a time period may be summed and then converted to activity points, or the activity points corresponding to any amounts of time that a person was not sleeping and/or sedentary during a time period may be summed.

At block 562, the device may subtract the fourth amount of activity (e.g., the sedentary activity time or corresponding points) from the sum of non-sedentary time or points at block 560. Because increments of time (e.g., the fourth amount) may correspond to negative activity points when the person was sedentary during that time, the sedentary time or points may be subtracted (or the negative points may be included in the sum of all activity amounts). The device may include multiple sedentary activity amounts in the overall sum, whether by adding all sedentary amounts and subtracting the summed sedentary amount from the summed non-sedentary amount, or by subtracting the individual sedentary amounts from the individual non-sedentary amounts.

At block 564, the device may determine an activity score for the time period based on the sum and subtraction (e.g., the sum of the positive activity points for the non-sedentary activity amounts, and the negative activity points for the sedentary activity amounts). For example, five minutes of intense activity may result in 10 points; four hours and thirty-five minutes of moderate activity may result in 275 points; one hour and thirty-nine minutes of light activity may result in one point; and fifteen hours and six minutes of sedentary time may result in negative thirty-six points. The activity score of 250 points may be the sum of the ten points, the 275 points, the 1 point, and the negative thirty-six points. In this manner, the activity score may account for multiple quantities of multiple levels of activity over time, the activity quantities and levels determined using a combination of device data and biometric data.

At block 566, the device may determine whether the activity score satisfies a score threshold (e.g., a goal score). The goal score may be set by the person for whom the activity score is calculated, may be determined by the device based on past activity data/scores for the person, or may be selected from a template. For example, a template may set the HR and motion thresholds and their correlation with different activity intensity levels, and the device may select a template randomly or based on information about the person, such as the person's age and/or health, and/or based on environmental information, such as a time of year (e.g., a month or season), weather, and the like. Satisfying the score threshold may refer to whether the activity score is above or below the goal score. For example, when the activity score is 250 points and the goal score is 300 points, the device may determine that the person needs 50 additional points to achieve the goal score, and may proceed to block 568. When the goal score is 250 points or less, then the device may determine that the activity score of 250 points has been met, and may proceed to block 570. The activity score may be for an entire duration (e.g., for a week of activity), or may indicate whether a person is on pace for the duration (e.g., whether the person scored enough activity points in a respective day to be on pace to reach a weekly goal). In this manner, the activity score data may provide real-time update to the user to provide incremental goals and feedback that may allow a user to achieve an activity goal.

At block 568, when the activity score has not reached the goal score (e.g., the person needs more activity points to achieve the goal score), the device may present, or send to another device for presentation, an indication that the activity score does not satisfy the score threshold (e.g., goal score). An example of this scenario is shown in FIG. 1, where the goal score is 300 points, and the activity score is 250 points. The device may present, or send to another device for presentation, the activity score, the goal score, and the remaining number of activity points (and/or corresponding amounts of activity at different activity intensity levels) that the person needs to achieve the goal score and satisfy the score threshold. The device may present, or send to another device for presentation, the activity score, the first, second, third, and fourth amounts of activity and/or the activity points corresponding to the first, second, third, and fourth amounts of activity. Block 568 may provide a real-time update that indicates that the person has not scored a number of activity points (e.g., for a day) to be on pace to achieve the goal score (e.g., for a week).

At block 570, when the activity score has reached the goal score (e.g., the person has exercised enough to meet or exceed the score threshold), the device may present, or send to another device for presentation, the activity score, the goal score, an indication that the activity score has met or exceeded the goal score, the time at which the activity score met or exceeded the goal score, the first, second, third, and fourth amounts of activity and/or the activity points corresponding to the first, second, third, and fourth amounts of activity. Block 570 may provide a real-time update that indicates that the person has scored a number of activity points (e.g., for a day) to be on pace to achieve the goal score (e.g., for a week).

In one or more embodiments, based on the activity score and whether the activity score exceeded the goal score, the device may adjust thresholds of a template, generate a new template with different thresholds, and/or may select a different template with different thresholds for the next time period during which to determine the person's activity score. For example, when the person meets a goal score, the device may modify, generate, or select another template with thresholds that are higher (e.g., requiring more activity to achieve a high/vigorous intensity activity level) for the next activity evaluation time period. When the person fails to meet a goal score, the device may modify, generate, or select another template with thresholds that are lower (e.g., requiring less activity to achieve a high/vigorous intensity activity level) for the next activity evaluation time period. Alternatively or in addition, the device may use a different goal score (e.g., as determined by a template or otherwise) for the next activity evaluation time period. For example, when the person meets a goal score, the device may modify, generate, or select another template with a goal score that is higher for the next activity evaluation time period. When the person fails to meet a goal score, the device may modify, generate, or select another template with a goal score that is lower for the next activity evaluation time period.

Still referring to FIG. 5B, the amounts of activity at an activity intensity level may be based on user inputs. For example, not all activity may be identified by a device, such as whether a person was lifting weights or running. A person may not have a device to measure the person's activity at the time during which the person performed the activity, or the device may not be able to differentiate between all types of activity. In this manner, the device may receive user inputs with which the person may indicate an activity performed and a time period during which the person performed the activity. For example, when the person provides a user input to the device indicating a type of activity and a duration (e.g., that the person lifted weights for an hour), the device may determine activity points that correspond to the one hour of weight lifting activity, and may account for the weight lifting activity points when determining an activity score.

The descriptions herein are not meant to be limiting.

Figure 6:
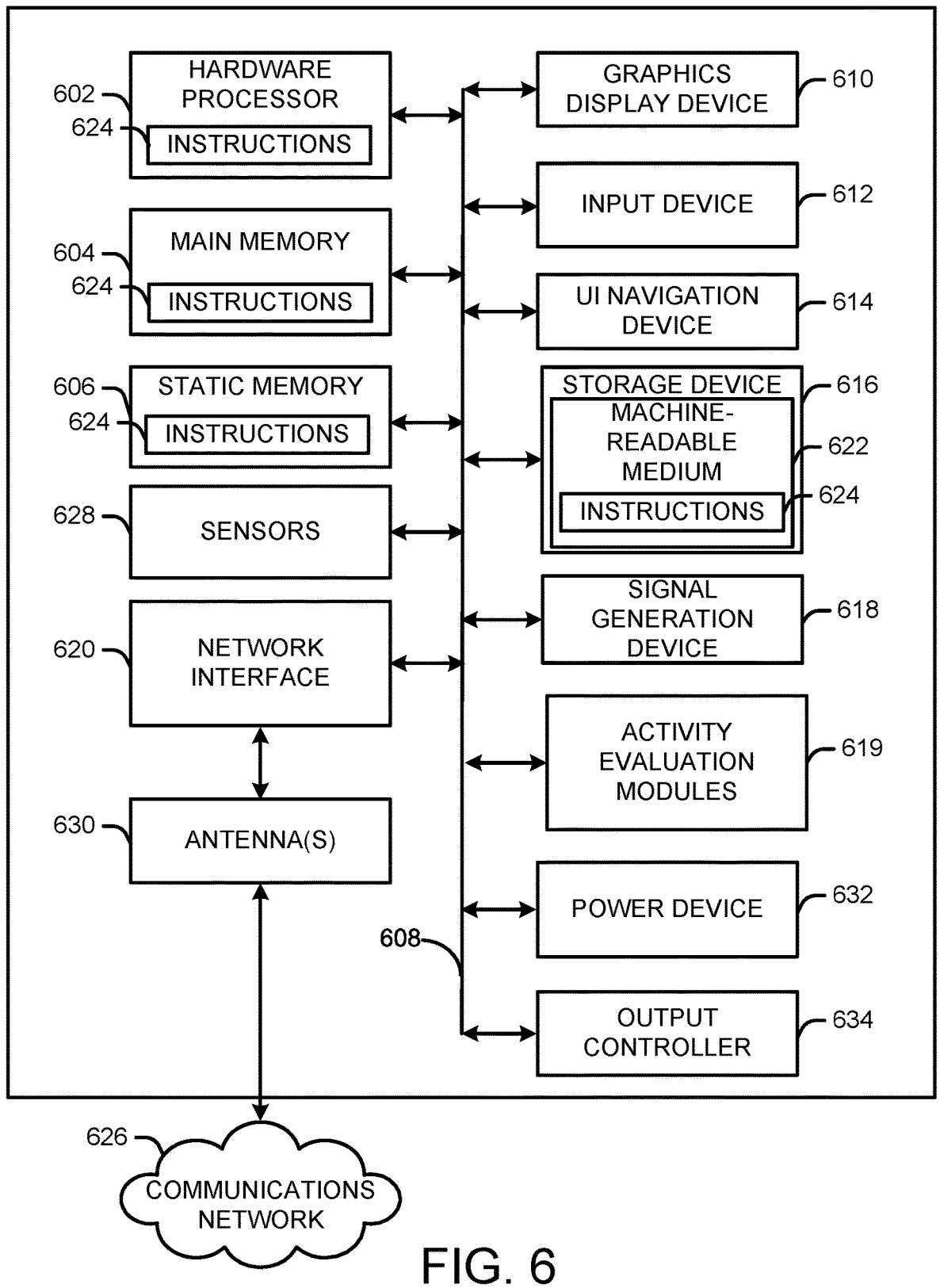
FIG. 6 illustrates a block diagram of an example machine upon which any of one or more techniques (e.g., methods) may be performed, in accordance with one or more example embodiments of the present disclosure.

FIG. 6 illustrates a block diagram of an example of a machine 600 (e.g., the device 104 of FIG. 1, the device 106 of FIG. 1, the device 108 of FIG. 1, the one or more servers 140 of FIG. 1) or system upon which any one or more of the techniques (e.g., methodologies) discussed herein may be performed. In other embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in Wi-Fi direct, peer-to-peer (P2P), cellular, (or other distributed) network environments. The machine 600 may be a server, a personal computer (PC), a smart home device, a tablet PC, a set-top box (STB), a personal digital assistant (PDA), a mobile telephone, a wearable computer device, a web appliance, a network router, a switch or bridge, or any machine capable of executing instructions (sequential or otherwise) that specify actions to be taken by that machine, such as a base station. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the execution units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a power management device 632, a graphics display device 610, an alphanumeric input device 612 (e.g., a keyboard), and a user interface (UI) navigation device 614 (e.g., a mouse). In an example, the graphics display device 610, alphanumeric input device 612, and UI navigation device 614 may be a touch screen display. The machine 600 may additionally include a storage device (i.e., drive unit) 616, a signal generation device 618, one or more activity evaluation modules 619 (e.g., capable of performing steps according to the blocks of FIGS. 2-5), a network interface device/transceiver 620 coupled to antenna(s) 630, and one or more sensors 628, such as a HR sensor, a global positioning system (GPS) sensor, a compass, an accelerometer, or other biometric and/or motion sensor. The machine 600 may include an output controller 634, such as a serial (e.g., universal serial bus (USB), parallel, or other wired or wireless (e.g., infrared (IR), near field communication (NFC), etc.) connection to communicate with or control one or more peripheral devices (e.g., a printer, a card reader, etc.)).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within the static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine-readable medium" may include a single medium or multiple media (e.g., a centralized or distributed database, and/or associated caches and servers) configured to store the one or more instructions 624.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 600 and that cause the machine 600 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device/transceiver 620 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 602.11 family of standards known as Wi-Fi®, IEEE 602.16 family of standards known as WiMax®), IEEE 602.15.4 family of standards, and peer-to-peer (P2P) networks, among others. In an example, the network interface device/transceiver 620 may include one or more physical jacks (e.g., Ethernet, coaxial, or phone jacks) or one or more antennas to connect to the communications network 626. In an example, the network interface device/transceiver 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 600 and includes digital or analog communications signals or other intangible media to facilitate communication of such software.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments. The terms "computing device," "user device," "communication station," "station," "handheld device," "mobile device," "wireless device" and "user equipment" (UE) as used herein refers to a wireless communication device such as a cellular telephone, a smartphone, a tablet, a netbook, a wireless terminal, a laptop computer, a femtocell, a high data rate (HDR) subscriber station, an access point, a printer, a point of sale device, an access terminal, or other personal communication system (PCS) device. The device may be either mobile or stationary.

As used within this document, the term "communicate" is intended to include transmitting, or receiving, or both transmitting and receiving. This may be particularly useful in claims when describing the organization of data that is being transmitted by one device and received by another, but only the functionality of one of those devices is required to infringe the claim. Similarly, the bidirectional exchange of data between two devices (both devices transmit and receive during the exchange) may be described as "communicating," when only the functionality of one of those devices is being claimed. The term "communicating" as used herein with respect to a wireless communication signal includes transmitting the wireless communication signal and/or receiving the wireless communication signal. For example, a wireless communication unit, which is capable of communicating a wireless communication signal, may include a wireless transmitter to transmit the wireless communication signal to at least one other wireless communication unit, and/or a wireless communication receiver to receive the wireless communication signal from at least one other wireless communication unit.

As used herein, unless otherwise specified, the use of the ordinal adjectives "first," "second," "third," etc., to describe a common object, merely indicates that different instances of like objects are being referred to and are not intended to imply that the objects so described must be in a given sequence, either temporally, spatially, in ranking, or in any other manner.

Some embodiments may be used in conjunction with various devices and systems, for example, a personal computer (PC), a desktop computer, a mobile computer, a laptop computer, a notebook computer, a tablet computer, a server computer, a handheld computer, a handheld device, a personal digital assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless access point (AP), a wired or wireless router, a wired or wireless modem, a video device, an audio device, an audio-video (A/V) device, a wired or wireless network, a wireless area network, a wireless video area network (WVAN), a local area network (LAN), a wireless LAN (WLAN), a personal area network (PAN), a wireless PAN (WPAN), and the like.

Some embodiments may be used in conjunction with one way and/or two-way radio communication systems, cellular radio-telephone communication systems, a mobile phone, a cellular telephone, a wireless telephone, a personal communication system (PCS) device, a PDA device which incorporates a wireless communication device, a mobile or portable global positioning system (GPS) device, a device which incorporates a GPS receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, digital video broadcast (DVB) devices or systems, multi-standard radio devices or systems, a wired or wireless handheld device, e.g., a smartphone, a wireless application protocol (WAP) device, or the like.

Some embodiments may be used in conjunction with one or more types of wireless communication signals and/or systems following one or more wireless communication protocols, for example, radio frequency (RF), infrared (IR), frequency-division multiplexing (FDM), orthogonal FDM (OFDM), time-division multiplexing (TDM), time-division multiple access (TDMA), extended TDMA (E-TDMA), general packet radio service (GPRS), extended GPRS, code-division multiple access (CDMA), wideband CDMA (WCDMA), CDMA 2000, single-carrier CDMA, multi-carrier CDMA, multi-carrier modulation (MDM), discrete multi-tone (DMT), Bluetooth®, global positioning system (GPS), Wi-Fi, Wi-Max, ZigBee, ultra-wideband (UWB), global system for mobile communications (GSM), 2G, 2.5G, 3G, 3.5G, 4G, fifth generation (5G) mobile networks, 3GPP, long term evolution (LTE), LTE advanced, enhanced data rates for GSM Evolution (EDGE), or the like. Other embodiments may be used in various other devices, systems, and/or networks.

It is understood that the above descriptions are for purposes of illustration and are not meant to be limiting.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in any applicable flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in any flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method, comprising:
receiving, by at least one processor of a first device or of a second device, body data of a user, the body data indicative of a heart rate associated with performance of an activity;
determining, by the at least one processor, and based on a comparison of the heart rate to a heart rate threshold, a threshold amount of motion;
determining, by the at least one processor, device accelerometer data;
determining, by the at least one processor and based on a comparison of the device accelerometer data to the threshold amount of motion, a threshold heart rate change;
determining, by the at least one processor, a heart rate change associated with the heart rate;
determining, by the at least one processor and based on a comparison of the heart rate change to the threshold heart rate change, an activity intensity level associated with the heart rate and the device accelerometer data;
determining, by the at least one processor and based on the activity intensity level, an activity score for the user; and
causing presentation, by the at least one processor, of data indicating the activity score.

2. The method of claim 1, wherein the heart rate is a first heart rate associated with performance of a first activity during a first time period, wherein the threshold amount of motion for the first time period is a first threshold amount of motion for the first time period, wherein the device accelerometer data is first device accelerometer data, wherein the threshold heart rate change is a first threshold heart rate change, wherein the heart rate change is a first heart rate change, and wherein the activity intensity level is a first activity intensity level, the method further comprising:
determining a second heart rate associated with performance of a second activity during a second time period;
determining, based on the second heart rate, a second threshold amount of motion for the second time period;
determining second device accelerometer data;
comparing the second device accelerometer data to the second threshold amount of motion;
determining, based on the comparison of the second device accelerometer data to the second threshold amount of motion, a second threshold heart rate change;
determining a second heart rate change associated with the second heart rate and the second time period; and
determining, based on a comparison of the second heart rate change to the second threshold heart rate change, a second activity intensity level associated with the second heart rate and the second device accelerometer data, the second activity intensity level different than the first activity intensity level,
wherein the activity score is further based on the second activity intensity level.

3. The method of claim 1, further comprising:
determining a heart rate threshold; and
comparing the heart rate to the heart rate threshold,
wherein determining the threshold amount of motion is based on the comparison of the heart rate to the heart rate threshold.

4. The method of claim 1, wherein the activity score is a first activity score associated with the user and performance of the activity during a first time period, the method further comprising determining a second activity score associated with the user and performance of a second activity during a second time period, the second time period occurring before the first time period, wherein determining the threshold amount of motion for the first time period is further based on the second activity score.

5. A method, comprising:
receiving, by at least one processor of a first device or of a second device, body data indicative of a heart rate of a user;
determining, by the at least one processor, and based on a comparison of the heart rate to a heart rate threshold, a motion threshold;
determining, by the at least one processor, motion data;
comparing, by at least one processor, the motion data to the motion threshold;
determining, by the at least one processor, based on the comparison of the motion data to the motion threshold and based on a comparison of a heart rate change associated with the heart rate to a threshold heart rate change, an activity intensity level;
determining, by the at least one processor and based on the activity intensity level, an activity score for the user; and
causing presentation, by the at least one processor, of data indicating the activity score.

6. The method of claim 5, further comprising:
determining, based on the comparison of the motion data to the motion threshold, the threshold heart rate change; and
determining the heart rate change, wherein the heart rate change is associated with a time period.

7. The method of claim 5, further comprising:
comparing the activity score to a score threshold; and
determining that the activity score exceeds the score threshold,
wherein the data further indicates that the activity score exceeds the score threshold.

8. The method of claim 7, wherein the score threshold is a first score threshold, the method further comprising determining a second score threshold that is larger than the first score threshold.

9. The method of claim 5, further comprising:
comparing the activity score to a score threshold;
determining that the activity score is less than the score threshold; and
determining a difference between the activity score and the score threshold,
wherein the data further indicates that the activity score is less than the score threshold by the difference.

10. The method of claim 9, wherein the score threshold is a first score threshold, the method further comprising determining a second score threshold that is smaller than the first score threshold by an amount associated with the difference.

11. The method of claim 5, wherein the heart rate and the motion data are associated with the user, the method further comprising:
determining a second heart rate associated with the user;
determining second motion data associated with the user; and
determining a second activity intensity level associated with the second heart rate and the motion data, the second activity intensity level different than the activity intensity level,
wherein determining the activity score is further based on the second activity intensity level.

12. The method of claim 11, further comprising determining a sum of first points associated with the activity intensity level and second points associated with the second activity intensity level,
wherein determining the activity score is further based on the sum.

13. The method of claim 5, wherein the heart rate is a first heart rate associated with the user, the method further comprising:
determining a second heart rate associated with the user;
determining second motion data associated with the user; and
determining a second activity intensity level associated with the second heart rate and the motion data, wherein the second activity intensity level indicates that the user was sedentary during a time period associated with the second heart rate; and
determining a subtraction of the activity score based on the second activity intensity level.

14. The method of claim 5, wherein the activity score is a first activity score associated with a first time period, wherein the heart rate is associated with the user, and wherein determining the heart rate threshold is based on at least one of data associated with the user or environmental data, wherein the data associated with the user comprises at least one of a user age or a second activity score associated with a second time period preceding the first time period.

15. The method of claim 5, further comprising:
receiving a user input comprising a type of activity and a duration associated with the activity; and
determining a second activity intensity level based on the user input,
wherein determining the activity score is further based on the second activity intensity level.

16. The method of claim 5, wherein the activity score is a first activity score associated with a first time period, the method further comprising:
determining a second activity score associated with a second time period preceding the first time period,
wherein determining the first activity score is further based on the second activity score.

17. The method of claim 5, wherein the heart rate and the motion data are associated with the user, a first time period, and a first heart rate change, and wherein the motion data is first motion data, the method further comprising:
determining a second heart rate associated with the user and a second time period;
determining second motion data associated with the user and the second time period;
determining, based on the second motion data, a threshold heart rate change for the second time period;
determining a second heart rate change associated with the second heart rate and the second time period; and
determining, based on a comparison of the second heart rate change to the threshold heart rate change, a second activity intensity level associated with the second heart rate and the second motion data, the second activity intensity level different than the activity intensity level,
wherein:
determining the activity score is further based on the second activity intensity level, and
at least one of the following:
the heart rate is different than the second heart rate,
the first motion data is different than the second motion data, or
the first heart rate change is different than the second heart rate change.

18. The method of claim 5, wherein the at least one processor is of a second device remote from the first device.

19. A system comprising:
memory coupled to at least one processor, the at least one processor configured to:
receive body data indicative of a heart rate for a time period;
determine, based on a comparison of the heart rate to a heart rate threshold, a motion threshold;
determine device data associated with a second device and a user;
compare the device data to the motion threshold for the time period;
determine, based on the comparison of the device data to the motion threshold, a heart rate change associated with the heart rate and the time period;
determine, based on a comparison of the heart rate change to a threshold heart rate change, an activity intensity level associated with the heart rate and the device data;
determine, based on the activity intensity level, an activity score for the user; and
send data indicating the activity score for the user for presentation at the second device.

20. The system of claim 19, further comprising a heart rate sensor of a first device, the heart rate sensor configured to detect the body data, and wherein the memory and at least one processor are of a second device remote from the first device.

\* \* \* \* \*